US00PP24277P3

(12) United States Plant Patent
Olesen

(10) Patent No.: US PP24,277 P3
(45) Date of Patent: Mar. 4, 2014

(54) COMPACT FLORIBUNDA ROSE PLANT NAMED 'POULCAS039'

(50) Latin Name: ***Rosa* hybrid**
Varietal Denomination: Poulcas039

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/507,025

(22) Filed: May 31, 2012

(65) Prior Publication Data

US 2013/0326761 P1 Dec. 5, 2013

(51) Int. Cl.
*A01H 5/00* (2006.01)

(52) U.S. Cl.
USPC ..... Plt./145

(58) Field of Classification Search
USPC ..... Plt./145
See application file for complete search history.

*Primary Examiner* — Kent L Bell

(57) ABSTRACT

A new garden rose plant of the Compact Floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas039'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulcas039', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas039' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcas039' was selected in the spring of 2005 by the inventor as a single plant from the progeny of the aforementioned hybridization.

Asexual reproduction of 'Poulcas039' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcas039' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas039'.

Specifically illustrated in FIG. 1 are flowers at various stages of development, flower in parts, leaves, and stems.

DETAILED DESCRIPTION OF THE VARIETY

Figure 1:
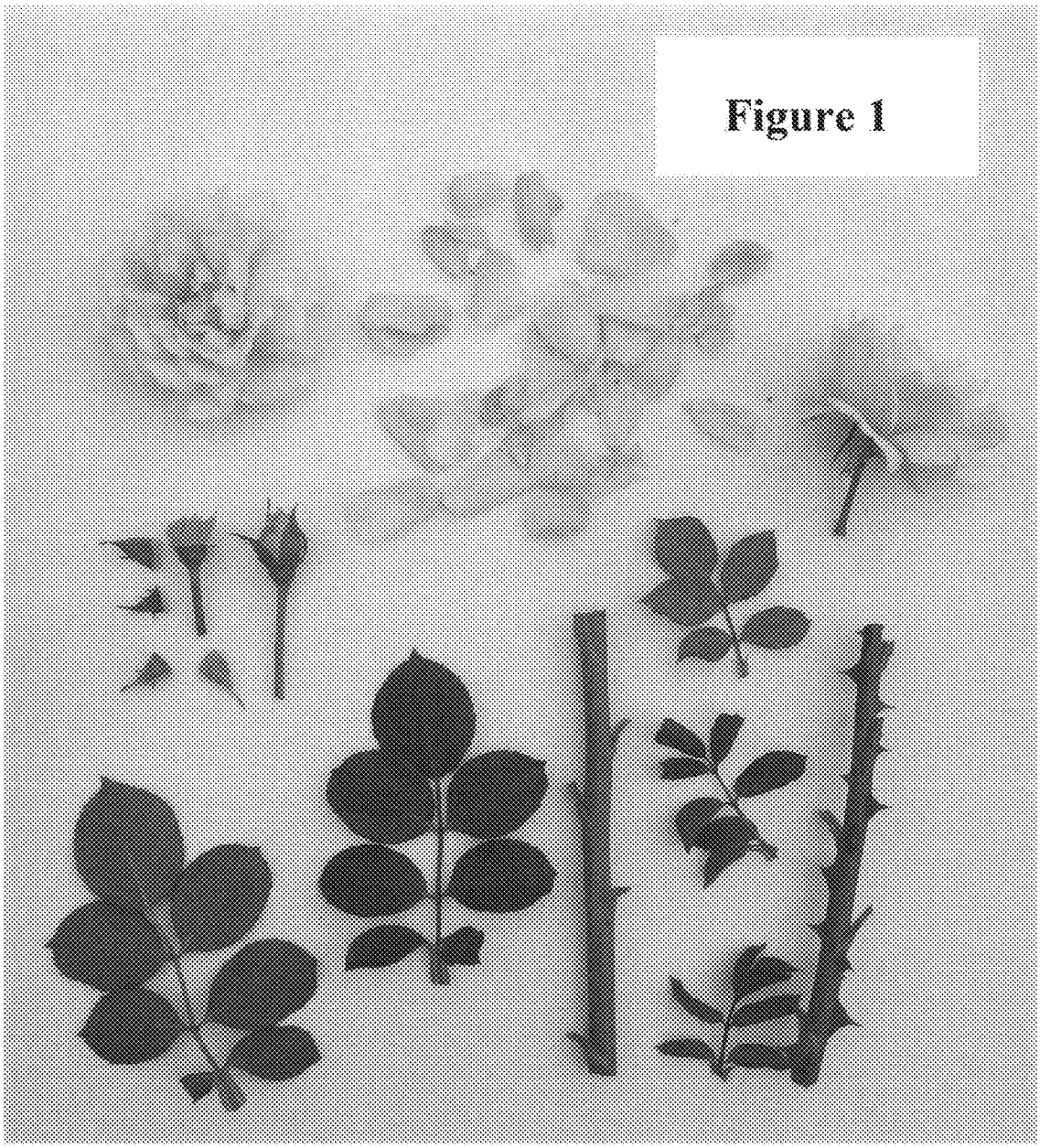
Figure 2:
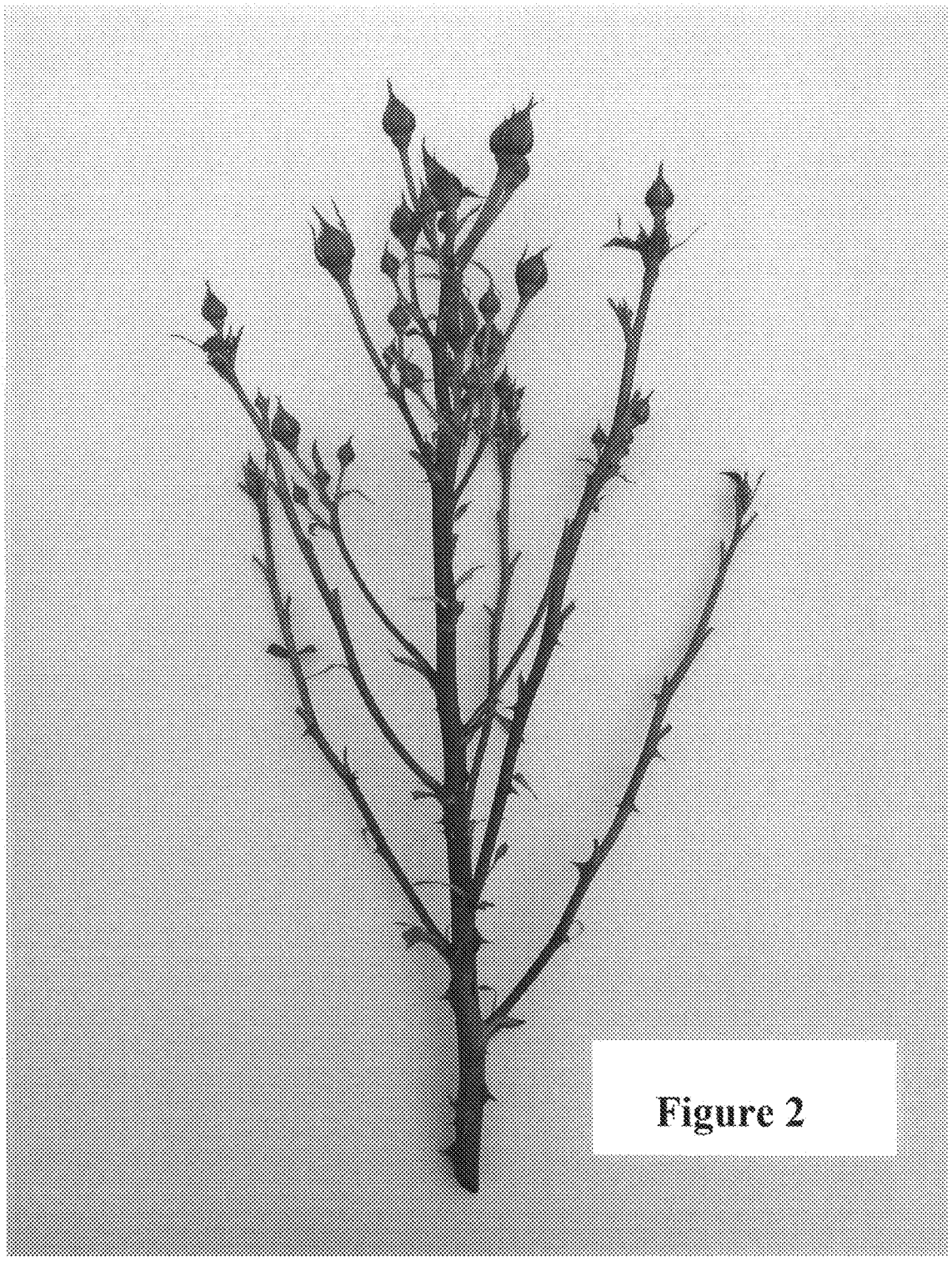
FIG. 2 illustrates the arrangement of peduncles and flowers on a flowering branch.

The following is a description of 'Poulcas039', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulcas018', U.S. Plant Pat. No. 16,991 are compared to 'Poulcas039' in Chart 1.

CHART 1

| | 'Poulcas039' | 'Poulcas018' |
|---|---|---|
| Petal Count | 50 petals | 130 |
| Flower Diameter | 70 to 75 mm | 50 mm |
| General Tonality of Flower Color | Yellow Group 5D and 9C. | Yellow Group 4D with intonations of 4C |

Flower and Flower Bud

Blooming habit: Continuous.

Flower bud:

*Size.*—Upon opening, 25 mm in length from base of receptacle to end of bud. Bud diameter is 15 mm.

*Bud form.*—Urceolate.

*Bud color.*—As sepals divide Orange Group 24B and Yellow Group 13C.

*Sepal inner surface.*—Color: Green Group 138B. Surface: Smooth with strong pubescence.

*Sepal outer surface.*—Color: Yellow-Green Group 144A with Greyed-Orange Group 173A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—23 mm long by 10 mm wide.

*Receptacle.*—Texture: Smooth. Size: 8 mm in height by 8 mm wide. Color: Yellow-Green Group 144A. Shape: Campanulate.

*Pedicel.*—Surface: Smooth with a few stipitate glands. Length: 30 to 40 mm. Diameter: 3 mm on average. Color: Yellow-Green Group 145A with anthocyanic pigments the color of Greyed-Red Group 182A observed. Strength: Moderate.

*Peduncle.*—Length: 1 cm to 25 cm. Diameter: 3 to 4 mm. Color: Yellow-Green Group 145A with Greyed-Red Group 182A.

Flower bud development: Flower buds are borne in clusters of about 5 flower buds per stem, resembling a panicle.

Flower bloom:

*Fragrance.*—Strong, citrus perfume.

*Duration.*—The blooms have a duration on the plant of approximately 10 days. Petals fall cleanly away from plant after flowers have fully matured.

*Size.*—Flower diameter is 70 to 75 mm when open. Flower depth is 30 mm.

*Flower shape.*—General shape is an open cup with petals that curve out from the center.

*Shape of flower, side view.*—Upon opening the upper portion is flat. The lower portion is a flattened convex.

Petalage: Under normal conditions, flowers have 50 petals total, 7 of which are petaloids.

General tonality of flower: Open flowers are Yellow Group 5D and 9C. Tonality changes to Yellow Group 4D as the flower ages.

Petal color:

*Upon opening, outer petals.*—Upper surface: Yellow Group 6D. Lower surface: Yellow Group 10D.

*Upon opening, inner petals.*—Upper surface: Yellow Group 10A. Lower surface: Yellow Group 11B.

*After opening, outer and inner petals.*—Upper surface: Yellow Group 4D with intonations of Yellow Group 5C at the basal zone. Lower surface: Yellow Group 4C and 4D.

*Petals.*—Petal reflex. — Somewhat reflexed to flat.

*Margin.*—Entire and uniform. Moderate undulations of margin observed.

*Shape.*—Generally narrow elliptic. Apex shape: Rounded. Base shape: Acute.

*Size.*—40 mm (l)×35 mm (w).

*Texture.*—Smooth.

*Thickness.*—Average.

Petaloids:

*Size.*—15 mm (l) by 5 mm (w).

*Quantity.*—7 on average.

*Shape.*—Symmetric, elliptic with a rounded apex and an acute base.

*Color.*—Upper surface is Yellow Group 4D with intonations of Yellow Group 5C at the basal zone. The lower surface is Yellow Group 4C and 4D.

Reproductive organs:

*Pollen.*—None observed.

*Anthers.*—Size: 2 mm in length. Color: Yellow Group 11B. Quantity: 75 on average.

*Filaments.*—Color: Yellow Group 12A. Length: 5 mm.

*Pistils.*—Length: 4 mm. Quantity: 45 on average.

*Stigmas.*—Color: Greyed-Yellow Group 160A.

*Styles.*—Color: Green-White Group 157A.

*Location of stigmas.*—Inferior in location relative to the length of the filaments and the height of the anthers.

*Hips.*—None Observed.

Plant

Plant growth: Upright, bushy. Plants are 50 cm in height, and 45 cm wide.

Stems:

*Color.*—Juvenile growth: Yellow-Green Group 144B with Greyed-Orange Group 174A. Mature growth: Yellow-Green Group 144B.

*Length.*—On average, canes are 35 cm from the base of the plant to the flowering portion.

*Diameter.*—5 mm.

*Internodes.*—On mature canes 25 to 30 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 7 mm.

*Shape.*—Upper portion is concave. Lower portion is concave.

*Color.*—Juvenile prickles: Greyed-Red Group 179A. Mature prickles: Greyed-Yellow Group 161A.

Plant foliage:

*Compound leaf.*—130 mm (l)×100 mm (w).

*Quantity.*—3 leaves per 10 cm of stem on average.

*Leaf bearing angle to the stem.*—45 degrees.

*Color of juvenile foliage.*—Upper side: Yellow-Green Group 144A with Greyed-Purple Group 183C at margins. Lower side: Greyed-Purple Group 183A.

*Color of mature foliage.*—Upper side: Yellow-Green Group 147A. Lower side: Yellow-Green Group 146B.

Plant leaves and leaflets:

*Stipules.*—Size: 20 mm in length. Quantity: 2 per compound leaf. Shape: Linear, slightly broad based with outward extending apices. Margins: Finely serrated with many stipitate glands. Color: Yellow-Green Group 144B.

*Petiole.*—Length: 15 to 25 mm. Diameter: 2 mm.

*Upper surface.*—Color: Yellow-Green Group 144A.

*Lower surface.*—Color: Yellow-Green Group 144B. Observations: Few stipitate glands and prickles observed.

*Rachis.*—Length: 30 to 45 mm. Upper surface: Color: Yellow-Green Group 144A.

*Lower surface.*—Color: Yellow-Green Group 144B. Observations: Few stipitate glands and prickles observed.

*Leaflet.*—Quantity: Normal number of leaflets per leaf in middle of the stem is 5 leaflets. Margins: Serrated. Size: Average size of the terminal leaflet on normal leaves is 55 mm in length by 45 mm wide. Shape: Generally oval. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulcas039', substantially as illustrated and described herein, due to its abundant yellow flowers, disease resistance, and extended period of bloom.

* * * * *